(12) United States Patent
Whiting et al.

(10) Patent No.: US 12,214,125 B2
(45) Date of Patent: Feb. 4, 2025

(54) DISTINGUISHING BETWEEN CENTRAL AND OBSTRUCTIVE SLEEP APNEA

(71) Applicant: Fisher & Paykel Healthcare Limited, Auckland (NZ)

(72) Inventors: David Robin Whiting, Auckland (NZ); Amol Man Malla, Auckland (NZ); Simei Gomes Wysoski, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 889 days.

(21) Appl. No.: 17/303,161

(22) Filed: May 21, 2021

(65) Prior Publication Data
US 2021/0338951 A1  Nov. 4, 2021

Related U.S. Application Data

(63) Continuation of application No. 16/520,194, filed on Jul. 23, 2019, now Pat. No. 11,040,159, which is a
(Continued)

(51) Int. Cl.
*A61M 16/00* (2006.01)
*A61B 5/00* (2006.01)
*A61B 5/087* (2006.01)

(52) U.S. Cl.
CPC ......... *A61M 16/0069* (2014.02); *A61B 5/087* (2013.01); *A61B 5/4818* (2013.01); *A61B 5/4836* (2013.01); *A61B 5/7267* (2013.01); *A61M 16/026* (2017.08); *A61M 2016/0027* (2013.01); *A61M 2016/003* (2013.01);
(Continued)

(58) Field of Classification Search
CPC ............ A61M 16/0068; A61M 16/024; A61M 16/026; A61M 16/022; A61M 16/0051; A61M 2016/0027; A61M 2016/003–0039; A61B 5/087; A61B 5/4818; A61B 5/4836; A61B 5/7264; A61B 5/7267; A61B 5/7282
See application file for complete search history.

(56) References Cited

U.S. PATENT DOCUMENTS 5,803,066 A * 9/1998 Rapoport .......... A61M 16/0069
                                                              128/207.18
6,739,335 B1    5/2004 Rapoport et al.
(Continued)

FOREIGN PATENT DOCUMENTS

EP     1150732       11/2001
EP     2008581 A2   12/2008
(Continued)

*Primary Examiner* — Valerie L Woodward
(74) *Attorney, Agent, or Firm* — Knobbe, Martens, Olson & Bear, LLP

(57) ABSTRACT

Apparatuses and methods for detecting sleep apnea and classifying the events as obstructive sleep apnea (OSA) and/or central sleep apnea (CSA) are disclosed herein. The apparatuses can include respiratory treatment devices that have an auto adjusting algorithm that is able to classify a sleep apnea as CSA or OSA so that an appropriate pressure can be applied to the patient depending on the type of sleep apnea detected. The apparatuses and methods can use characteristics of at least one breath preceding the apnea event in classifying the event.

20 Claims, 14 Drawing Sheets

Related U.S. Application Data continuation of application No. 14/785,291, filed as application No. PCT/IB2014/060787 on Apr. 17, 2014, now Pat. No. 10,406,306.

(60) Provisional application No. 61/813,081, filed on Apr. 17, 2013.

(52) U.S. Cl.
CPC .............. *A61M 2016/0036* (2013.01); *A61M 2205/3303* (2013.01); *A61M 2205/3334* (2013.01); *A61M 2205/50* (2013.01); *A61M 2230/40* (2013.01)

(56) References Cited

U.S. PATENT DOCUMENTS

| | | | |
|---|---|---|---|
| 7,370,650 | B2 | 5/2008 | Nadjafizadeh et al. |
| 7,413,549 | B1 | 8/2008 | Koh |
| 7,722,546 | B2 | 5/2010 | Madaus et al. |
| 10,406,306 | B2 | 9/2019 | Whiting et al. |
| 2004/0230105 | A1 | 11/2004 | Geva et al. |
| 2005/0074741 | A1 | 4/2005 | Lee et al. |
| 2007/0227539 | A1 | 10/2007 | Schwaibold et al. |
| 2008/0009755 | A1 | 1/2008 | Patangay et al. |
| 2008/0041382 | A1 | 2/2008 | Matthews et al. |
| 2008/0082018 | A1 | 4/2008 | Sackner et al. |
| 2008/0142011 | A1 | 6/2008 | Aylsworth et al. |
| 2008/0300500 | A1 | 12/2008 | Reisfeld |
| 2008/0302364 | A1 | 12/2008 | Garde et al. |
| 2009/0038617 | A1 | 2/2009 | Berthon-Jones et al. |
| 2011/0297156 | A1 | 12/2011 | Shelly et al. |
| 2012/0179061 | A1 | 7/2012 | Ramanan et al. |
| 2012/0227740 | A1 | 12/2012 | Berthon-Jones et al. |
| 2013/0324877 | A1 | 12/2013 | Nonaka et al. |
| 2014/0188006 | A1* | 7/2014 | Alshaer .................. A61B 7/003 600/586 |

FOREIGN PATENT DOCUMENTS

| | | |
|---|---|---|
| EP | 113196 A2 | 11/2009 |
| FR | 2905063 A1 | 2/2008 |
| NZ | 552070 | 11/2008 |
| WO | WO 2012/155257 | 11/2012 |

* cited by examiner

DISTINGUISHING BETWEEN CENTRAL AND OBSTRUCTIVE SLEEP APNEA

INCORPORATION BY REFERENCE TO RELATED APPLICATIONS

This application is a continuation of U.S. patent application Ser. No. 16/520,194, filed Jul. 23, 2019, which is a continuation of U.S. patent application Ser. No. 14/785,291, filed Oct. 16, 2015, now U.S. Pat. No. 10,406,306 entitled "DISTINGUISHING BETWEEN CENTRAL AND OBSTRUCTIVE SLEEP APNEA", which is a national phase entry of PCT Application No. PCT/IB2014/060787, filed Apr. 17, 2014, entitled "DISTINGUISHING BETWEEN CENTRAL AND OBSTRUCTIVE SLEEP APNEA," which claims priority to U.S. Provisional Application No. 61/813,081, filed Apr. 17, 2013, entitled "APPARATUS AND TECHNIQUE FOR DISTINGUISHING BETWEEN CENTRAL AND OBSTRUCTIVE SLEEP APNEA". Any and all applications for which a foreign or domestic priority claim is identified above or in the Application Data Sheet as filed with the present application are hereby incorporated by reference under 37 CFR 1.57.

FIELD

The present disclosure generally relates to devices for treating sleep disorder breathing. More particularly, the present disclosure relates to devices capable of distinguishing between obstructive sleep apnea and central sleep apnea.

BACKGROUND

Respiratory disorders deal with the inability of a sufferer to effect a sufficient exchange of gases with the environment, leading to an imbalance of gases in the sufferer. These disorders can be attributed to a number of different causes. For example, the cause of the disorder may be (1) a pathological consequence of an obstruction of the airway, (2) insufficiency of the lungs in generating negative pressure, (3) an irregularity in the nervous function of the brain stem, or some other disorder. Treatment of such disorders is diverse and depends on the particular respiratory disorder being targeted.

In the first instance, a constriction of the airway, otherwise known as an obstructive apnea or a hypopnea, collectively referred to as obstructive sleep apnea (OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression, and anxiety.

Obstructive sleep apnea is commonly treated with the application of continuous positive airway pressure (CPAP) therapy. Continuous positive airway pressure therapy involves delivering a flow of gas to a patient at a therapeutic pressure above atmospheric pressure that will reduce the frequency and/or duration of apneas and/or hypopneas. This therapy is typically delivered by using a continuous positive airway pressure device (CPAP device) to propel a pressurized stream of air through a conduit to a patient through an interface or mask located on the face of the patient.

Central sleep apnea (CSA) is a type of sleep apnea where the patient stops breathing due to lack of respiratory drive from the brain. CSA is prevalent in approximately 3 to 6% of patients with sleep disorder breathing. However, CSA prevalence drops to about 1.5% after six weeks on CPAP therapy because some patients adapt to the CPAP therapy. Unlike OSA, there is no evidence to-date that CSA can be treated with an increase in positive airway pressure (PAP). On the contrary, some studies suggest that the increase in pressure provided by PAP can trigger additional events called induced CSA. When CSA is detected, it is currently recommended that there be no pressure change responses.

SUMMARY OF THE DISCLOSURE

Some respiratory treatment devices currently classify all sleep apnea it detects as an obstructive sleep apnea and increases the positive airway pressure appropriately to treat OSA. However, a patient with sleep disorder breathing can suffer from one or both of OSA or CSA. Thus, it is important to determine whether a particular apnea is caused by an obstruction or a neurological response so that an appropriate device reaction can be determined.

The present disclosure describes a CPAP device that includes an auto adjusting algorithm that is able to classify a sleep apnea as either a CSA or OSA or combination of both so that an appropriate pressure can be applied to the patient depending on the type of sleep apnea detected. In an embodiment, a passive machine with a learning algorithm can be used to derive a sleep apnea classifier model. The classifier can be derived from previously recorded data samples (training data). For example, flow signals can be collected during sleep periods of several patients. Of particular interest are the signals immediately before and after apnea events. The apnea events in the training data are labeled into apnea classes, such as, for example, OSA vs non-OSA, CSA vs non-CSA, OSA vs CSA.

In an embodiment, the determination of OSA or CSA is made by looking at a number of breaths that occur directly before an apnea event. In one embodiment, the 8 breaths that occurred prior to the apnea are analyzed. The pre-apnea breaths' morphology is analyzed to determine the characteristics of the breaths. The characteristics are compared to pre-determined data of patients experiencing known OSA and CSA events. The comparison information provides an indication of whether the patient is experiencing an OSA event or a CSA event. In an embodiment, the morphology characteristics of the pre-apnea breaths are combined to determine a final morphology score. In an embodiment, this score is a probability distribution. The score or probability distribution is then compared with threshold information determined from empirical data to determine if the apnea is an OSA or CSA apnea.

BRIEF DESCRIPTION OF THE DRAWINGS

These and other features, aspects and advantages of the present disclosure will now be described with reference to the drawings of a preferred embodiment, which embodiment is intended to illustrate and not to limit the invention, and in which figures.

DETAILED DESCRIPTION

Certain features, aspects and advantages of the present disclosure relate to a method for automated adjustment of respiratory treatment devices, such as CPAP devices, and automated classification of sleep apnea type. In some configurations, the method can be implemented using a sleep apnea classification algorithm and an auto adjustment algorithm that are implemented and integrated as part of an overall CPAP control structure. An embodiment of a CPAP system and its corresponding major hardware components are described with respect to FIGS. 13 and 14.

As described herein, the sleep apnea classification algorithm can classify an apnea detected by the apnea detector as OSA or CSA by analyzing the characteristics of the breaths surrounding the apnea.

Figure 1:
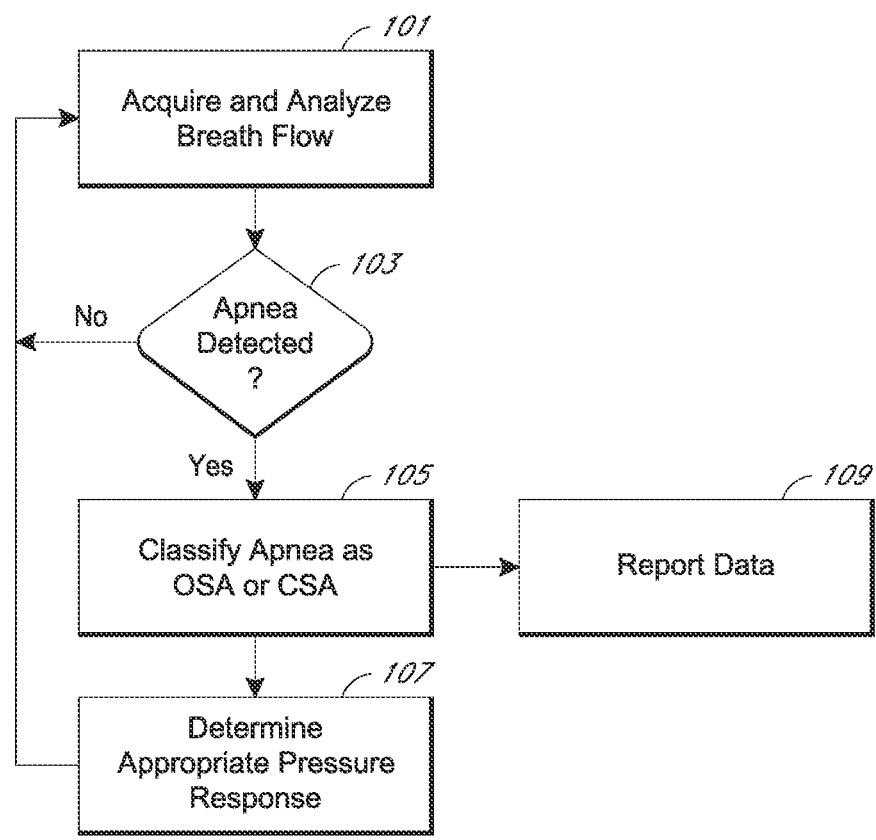
FIG. 1 is a high level flow chart of an OSA/CSA classification system.

FIG. 1 shows a flow chart of an embodiment of a process for determining whether an apnea should be classified as an OSA or CSA event. The process starts at step 101 where breath flow signals are acquired and analyzed by a device providing positive air flow pressure to a patient. The system periodically determines from the breath flow data at step 103 if an apnea has been detected. If an apnea has not been detected, the system continues to monitor the breath flow uninterrupted. If an apnea is detected at step 103, then the system moves to stop 105 where the apnea is classified as an OSA event or a CSA event. In an optional embodiment, the event information is reported at step 109. Also optionally, once the apnea is classified, the system can determine an appropriate pressure response at step 107. The system then returns to step 101 and continues to monitor the patient. At step 107, the pressure response can be an increase in pressure, a decrease in pressure, or no responsive pressure changes. In an embodiment, if the apnea is an OSA event, the pressure is increased. In an embodiment, if the apnea is a CSA event, the pressure is maintained or decreased. In an embodiment, if the apnea is a CSA event, the pressure is increased if a current pressure is below a CSA pressure limit. In an embodiment, the CSA pressure limit is about 10-20 cmH$_2$O. In other embodiments, the CSA pressure limit is about 12-15 cmH$_2$O.

Figure 1A:
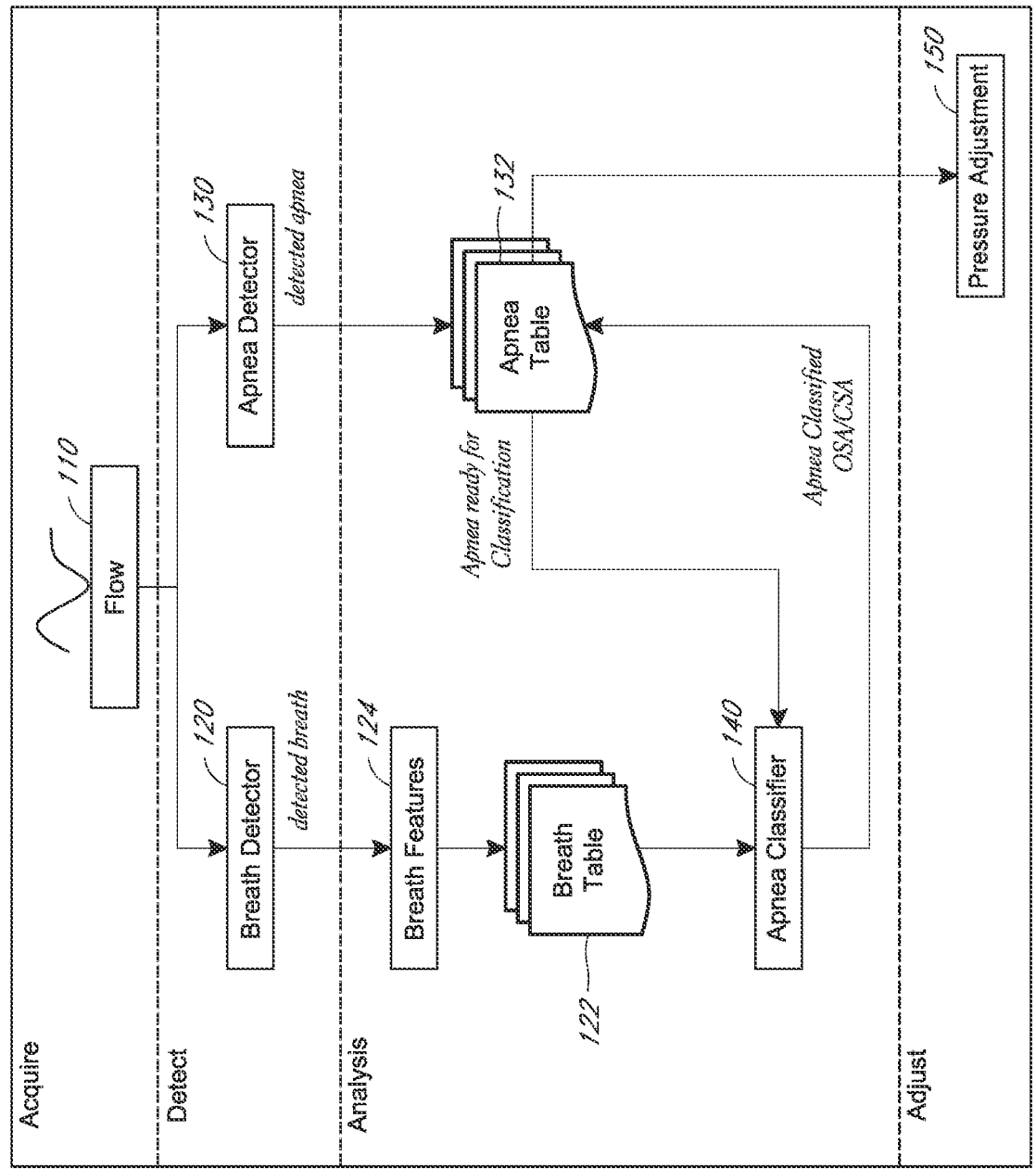
FIG. 1A is a flow diagram of an OSA/CSA determination embodiment of the disclosure.

FIG. 1A illustrates another embodiment of an apnea detection and classification system. In the first step, the flow data 110 is acquired. In the second step of the process, the acquired flow data is analyzed by breath detector 120 and apnea detector 130. The breath detector 120 determines individual and group breath information. The apnea detector determines if an apnea is believed to have occurred. The output of each detector can be stored into respective storage tables. When a breath is detected, information, such as any of a variety of breath features 124, can be determined and stored in a breath table 122. When an apnea is detected, the apnea information can be stored in an apnea table 132.

During the analysis phase, the apnea table 132 is regularly checked, for example, after every valid breath, for a detected apnea that is ready to be classified. An apnea is considered ready to be classified if a pre-defined number of expected breaths (such as, for example, one breath or a group of breaths in certain implementations) or period of time has passed since the apnea was detected. The apnea then can be classified by the apnea classifier 140 using information from the breath table 122 and apnea table 132. The apnea can be classified into an OSA class or a CSA class or another appropriate class.

Figure 2:
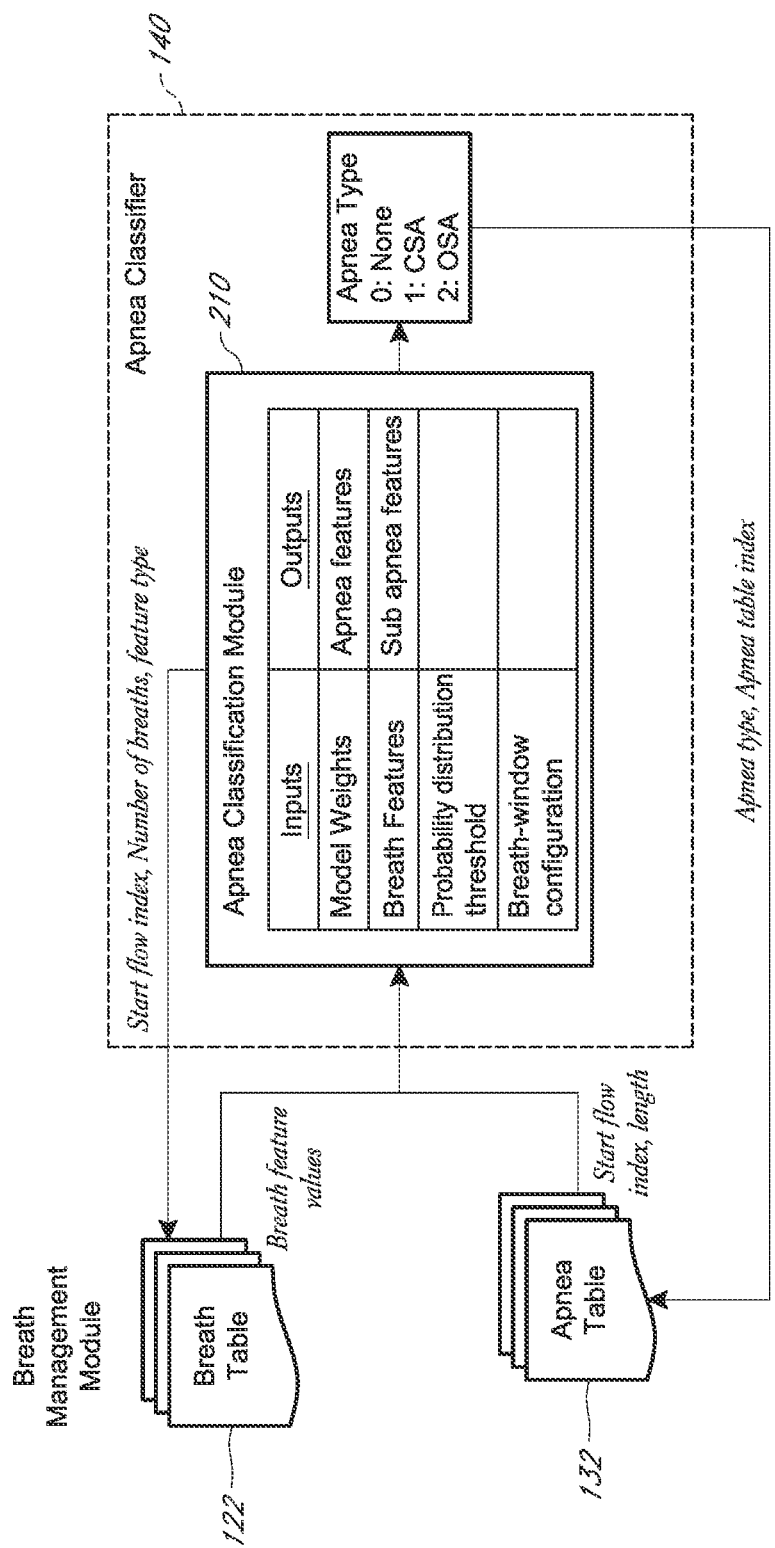
FIG. 2 is a flow diagram illustrating additional details of the embodiment of FIG. 1A.

Finally, the optional pressure adjustment module 150 can use the class of the apnea to determine an appropriate pressure response for the detected apnea. In an embodiment, an apnea event can be deleted, or declared finished, from the apnea table 132 once the number of post apnea breaths for the apnea is greater than or equal to the maximum number of post apnea breaths that are stored (such as, for example, 1 or more breaths in certain implementations). This allows the system to move onto a new apnea event where the process is repeated FIG. 2 illustrates greater details of the apnea classifier 140. The apnea classifier 140 receives as inputs the parameters of an apnea in the apnea table 132 and the breath features of breath table 122 relevant to the apnea. The apnea classifier 140 uses the flow index analysis and a length of an apnea from the apnea table 132 to determine which breaths in the breath table 122 to use for apnea classification.

Once the corresponding breaths of an apnea are determined, the apnea classification module 210 of apnea classifier 140 can request information from the breath table 122. The breath information obtained from the breath table 122 is used in conjunction with the apnea information obtained from the apnea table 132 to classify the apnea. The apnea classifier outputs the predicted type of the apnea. The apnea type is fed back to the apnea table 132 where it can be stored in an apnea type field entry of the respective apnea in the apnea table 132.

Figure 3:
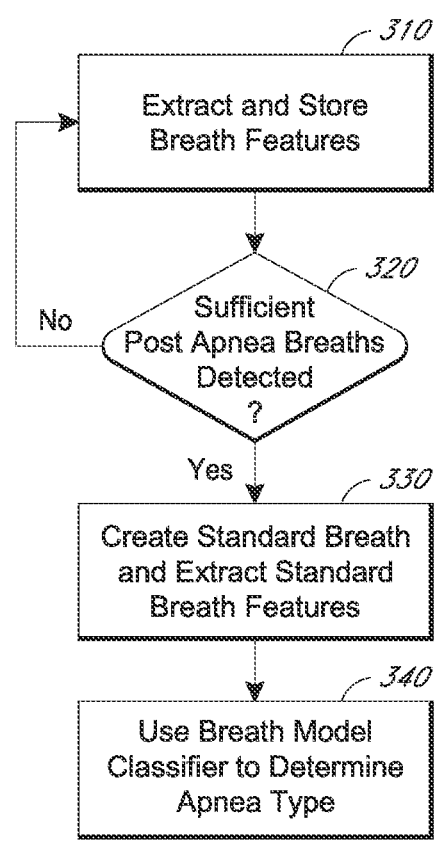
FIG. 3 is a flow chart of an apnea classification process.

With reference to FIG. 3, a flow chart for an apnea classification process is illustrated. The flow chart can be implemented as part of a breath analysis process of a CPAP device control software. This illustrated process is repeated throughout the sleep session. This process can be implemented as part of the processes described above with respect to FIGS. 1, 1A and 2.

FIG. 3 begins at step 310 where the system receives flow data and extracts and stores breath features. When an apnea is detected, the apnea classification can be carried out once the apnea is populated in the apnea table and enough valid breaths have passed since the detection of the apnea to indicate the conclusion or ending of the apnea as determined at step 320. In some embodiments of the apnea classification model, only pre-apnea breaths are analyzed to classify the apnea. As a result, in these embodiments, only a single or small number of post-apnea valid breaths may be needed before apnea classification. Alternatively, the classification can be performed once an apnea has been detected via an apnea detection algorithm and there is no need to wait until the first breath after the apnea to complete the classification. In other embodiments, additional post-apnea breaths are detected before the apnea is classified.

Once a sufficient number of post apnea breaths have been detected, the next step in the illustrated apnea classification process occurs at step 330 which involves creating a standard breath and extracting the breath features of the standard breath. The standard breath is determined in order to effectively normalize the detected breaths to make the system generally invariant to the scale of the flow data. The standard breath can be determined from either pre-apnea breath information, post-apnea breath information or both pre and post apnea breath information. In an embodiment, a group of pre-apnea breaths is used to determine the standard breath. In an embodiment 1 to 12 breaths are used. In an embodiment, 8 breaths are used. The use of only pre-apnea breaths in the determination of the apnea type allows the apnea classification to occur sooner because only one or a few post apnea breaths are necessary before the classification can occur. In such embodiments, because the apnea classification can occur more quickly than waiting for and analyzing post apnea breaths, pressure decisions can be made sooner, leading to a more responsive CPAP system.

In step 340, the apnea is classified by calculating the apnea features and then using those apnea features with an apnea classifier model to determine the apnea type. The method for the apnea feature calculation and apnea classification can be implemented in a module within the control software and will be further discussed below.

Figure 4:
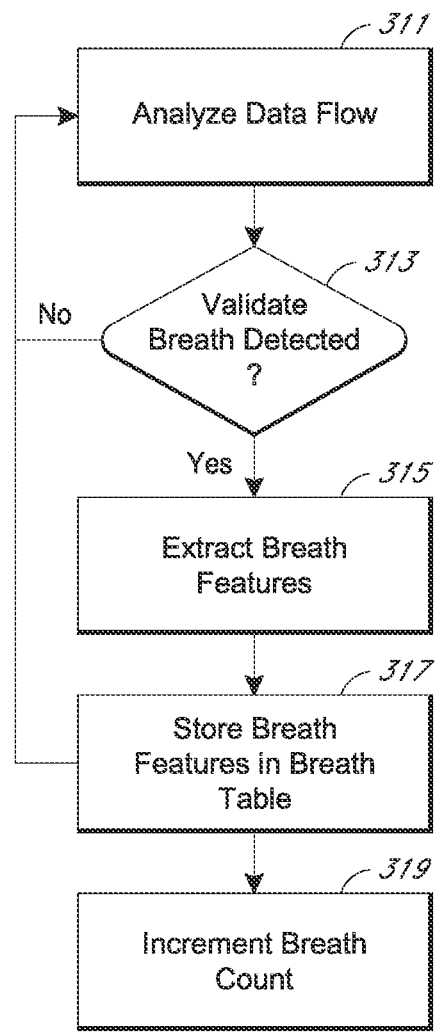
FIG. 4 is a flow chart of a breath feature extraction process.

FIG. 4 illustrates greater details of step 310 of FIG. 3. The process of step 310 begins at step 311 by first analyzing the flow data. The process then determines if a valid breath has been detected at step 313. If a valid breath is detected, then the morphological features of the breath are extracted at step 315. The extracted breath features are added to the breath table 122 at step 317. Optionally, at step 319 a breath count is incremented. The breath count can be the number of breaths recorded since the end of a previous apnea, the number of breaths recorded in a session or any other meaningful breath count. The morphological features analyzed are explained in greater detail herein below.

Standard Breath Determination

Standard breaths can be used for normalisation of the breath-features of the detected breaths because the scale of the flow data can significantly affect the classifier calculation. Scale differences occur due to a variety of uncontrollable factors including, for example, sensor sensitivity, patient physiology, pressure changes within the system, etc. The normalisation of breath-features with a local standard breath makes the apnea classification method generally invariant to the scale of the flow data. Breath features of each detected breath can be normalised by dividing it with a corresponding breath-feature of the standard breath.

A standard breath is a sinusoidal representation of average breath features derived from a local breath-window at a certain point in a time series. For apnea classification, the breath-window with a number of pre-apnea breaths can be used to derive average breath parameters to form a standard breath. In an embodiment, this can include a window containing the maximum number of pre-apnea available breaths. In an embodiment, the window contains a set number of breaths, for example, 8 breaths. However, under certain circumstances, such as when an apnea is detected just after an end of a CPAP mask leak, there might be less breaths in the breath table than required. In these cases, where the apnea classification function is not ready, the standard breath can be derived with the available pre-apnea breaths detected after the leak has stopped. In addition, breaths detected during apnea also can be excluded for derivation of the standard breath used during the apnea classification method.

Figure 5:
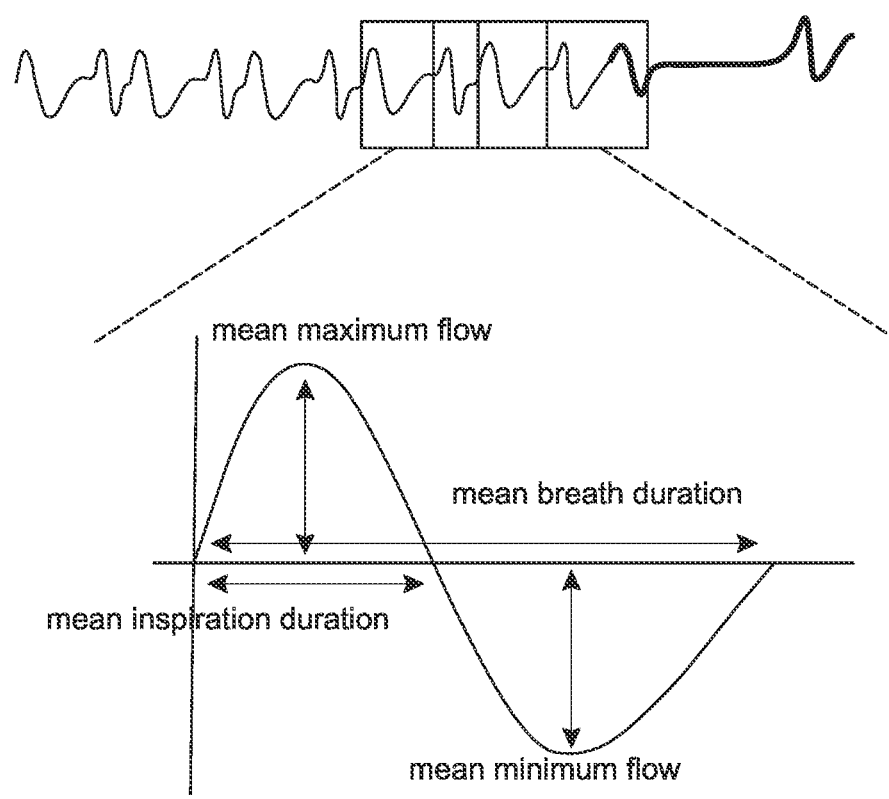
FIG. 5 is a graphical illustration of deriving a standard breath.

As shown in FIG. 5, the standard breath is derived by fitting two respective sinusoids to average inspiration and expiration measures of breaths in a pre-defined breath-window. The two sinusoids can be derived from the mean of maximum flow, the mean duration of inspiration, the mean minimum flow, and/or the mean total breath duration over the breath-window. Of course, other morphological features can be used to determine the standard breath, for example, any of the features listed in Table 1 below. Once the standard breath is derived, the breath features of the standard breath can be calculated in the same way or similar to every other detected breath.

Apnea Classification

The apnea classification module 210 contains the functions that are used to classify an apnea. In an embodiment, the process of apnea classification can involve extraction of the pre-apnea breath features, using the pre-apnea breath features with a model to calculate a probability distribution and finally deciding the class of an apnea by comparing the probability distribution to a predetermined threshold. The breath-window configuration and the parameters of the model can be defined in this module.

Any number of different models can be used with the present system. For example, a logistics model or simple logistics model can be used. In other embodiments, a neural network, multiple perceptron model or support vector machine model can be used. Of course, it is to be understood that other models or combinations of models can be used as well.

Apnea Feature Extraction

In some embodiments, the first step in classification of an apnea is to extract apnea features. Extraction of apnea features involves capturing static and/or temporal characteristics of a flow signal (including, for example, breath data) preceding and following a sleep apnea. The apnea features are derived by calculating statistical metrics of breath features within predefined breath-windows.

Apnea Windows

Figure 6:
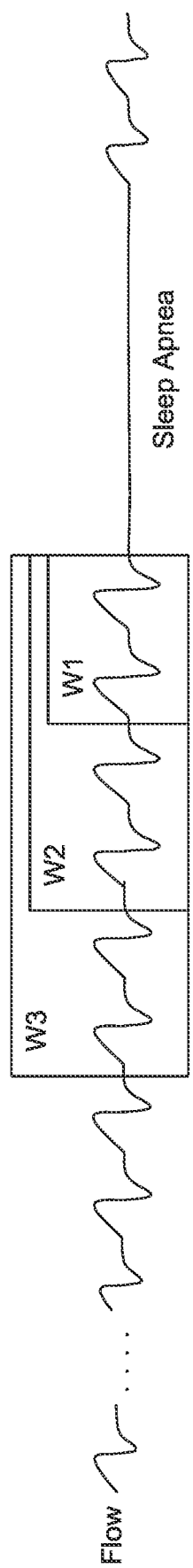
FIG. 6 is a diagram illustrating breath windows of pre-apnea breaths used for apnea feature extraction.

The process of apnea breath feature extraction can involve acquiring the breath-features for pre-defined breath-windows and then calculating the breath-feature statistics for each breath-window. A breath-window can be a pre-defined number of breaths either before and/or after a sleep apnea. The statistics of the breath-features within each breath-window capture characteristics of the flow signal during that period. The use of multiple breath-windows allows the capture of flow signal characteristics over different time periods. The apnea classification model can learn the difference in flow characteristics surrounding each apnea. FIG. 6 illustrates a breath-window configuration that consists of 3 pre-apnea breath-windows, W1, W2, and W3 with 2, 4, and 6 breaths respectively. Other breath window configurations could be used as well. For example, in an embodiment, 8 pre-apnea breaths are used with four different over lapping or independent windows. In an embodiment, the first window has two breaths, the second window has 4 breaths, the third window has six breaths and the fourth window has all eight breaths. Other configurations, numbers of windows or numbers of pre or post apnea breaths can also be used.

Although the configuration of FIG. 6 uses only the pre-apnea breath-windows, it is possible to use both pre-apnea and post-apnea breath-windows. Using both pre-apnea and post-apnea windows allows the capture of flow characteristics both before and after an apnea. However, one disadvantage of using a post-apnea window is that the pressure response to a detected apnea will be delayed because the classification of an apnea can only be performed once all the required post-apnea breaths have passed. Because of this delay in classification performance with the post-apnea window, some embodiments of the present disclosure only use pre-apnea windows. In some configurations, the software module can be implemented to be able to use pre and post apnea windows as well as only one of the pre and post apnea windows.

Determination of Start of Pre-Apnea Breath

For each breath-window, there is a determination of which breaths to use within the breath table. In some configurations, there are two criteria under which a breath may be excluded for apnea classification. For example, the breath may be avoided if: a breath turns into an apnea (apnea-breath); or a breath was detected during an apnea.

Figure 7:
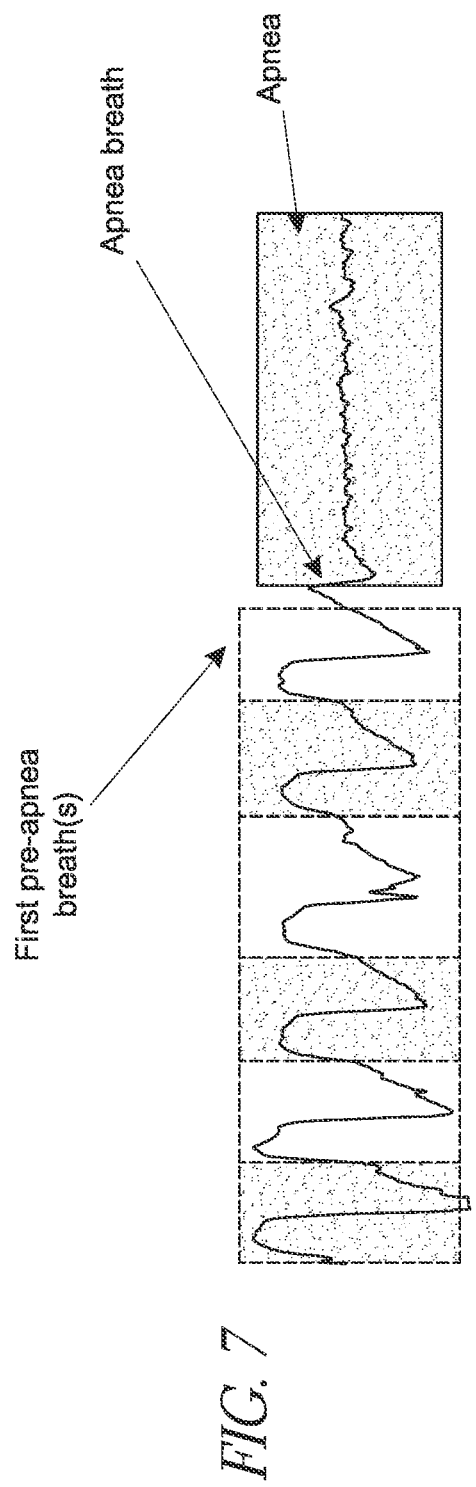
FIG. 7 is a graphical illustration of breaths in a pre-apnea breath window used for classification of an apnea.

The apnea-breath is determined by comparing the start and end flow index of an apnea and breaths in the breath table at the time the apnea was detected. By comparing the flow index of the end of the breath to the flow index of the start of the apnea in order of the newest breath to the oldest breath in the breath table, the newest breath after the apnea breath can be determined. In other words, the index (S) of the newest breath in the breath table, whose end of the breath flow index is less than the start of the apnea flow index, can be chosen as the start of the pre-apnea breath. Examples of the pre-apnea breaths used for apnea classification are shown in FIG. 7.

The newest pre-apnea breath defined by the breath table index S and breaths preceding it in the breath table are used for apnea classification.

Exclusion of Breaths During Apnea

In addition to the exclusion of the apnea-breaths, if a breath within an apnea breath-window is marked as a breath during an apnea (BDA), it is also not used for apnea classification. The BDA breaths can be considered to be a false detection of a breath because the presence of a breath during a sleep apnea generally is contradictory to the definition of a sleep apnea. In addition to the above reasons, BDA also may be avoided because they can produce extreme breath feature values (such as extremely long breath lengths), which can have undesirable effects on the apnea features because it is calculated based on the statistics of the breath-features in the breath-window.

Figure 8:
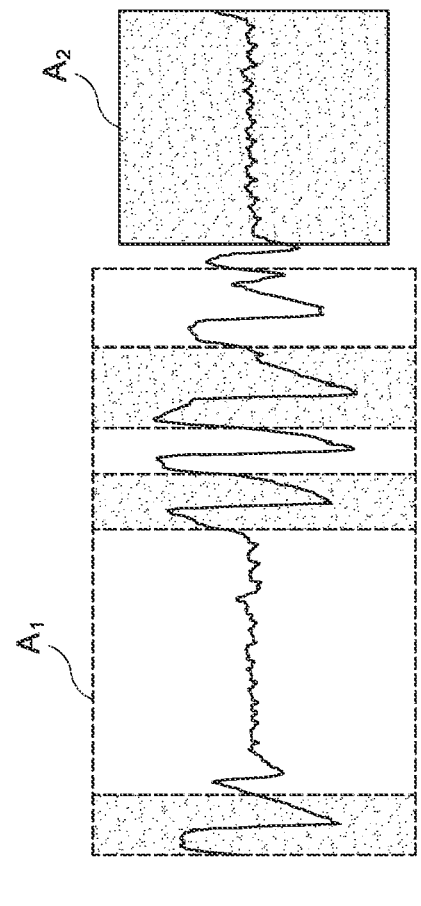
FIG. 8 is a graphical illustration of a breath during an apnea.

A BDA is most likely to be present within a breath-window if two or more apneas occur one after another with only few breaths between them. An example of a BDA breath when two apneas occur within 4 breaths of each other is illustrated in FIG. 8. In this example, the second BDA breath A1 is the apnea-breath of a preceding apnea to apnea A2.

Figure 9:
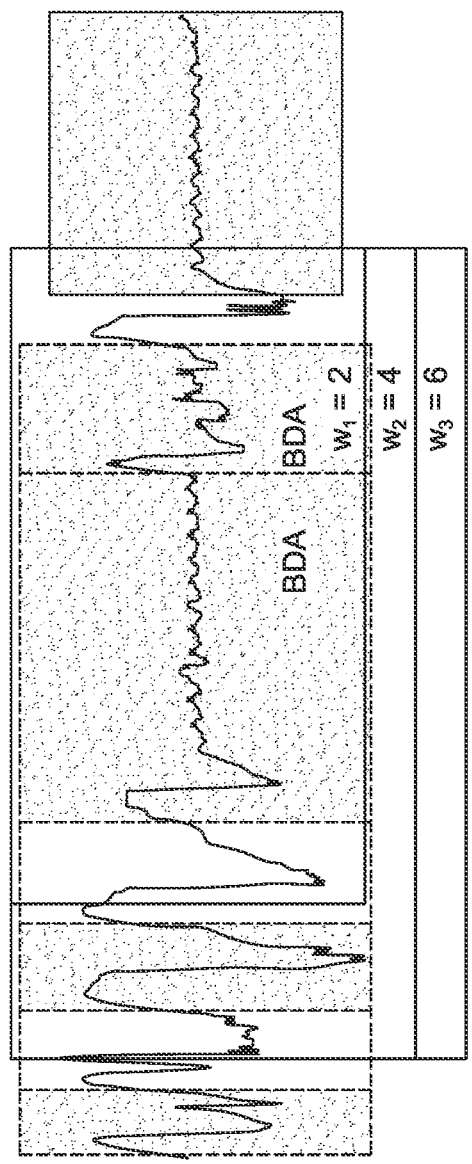
FIG. 9 is a graphical illustration of a breath-window configuration when breaths during an apnea are detected.

For a breath-window, if there is less than the required non-BDA breaths after the exclusion of the BDA breaths, the number of breaths in the breath-window can be increased either until there are enough none-BDA breaths or the number of breaths has reached the breaths size of the largest breath-window. For example, in FIG. 9, because the first breath-window (w1) requires 2 non-BDA breaths, the window size is increased to 4 because the 2 latest breaths are BDA breaths. Similarly, because the second breath-window (w2) requires 4 non-BDA breaths, its size is increased to 6 breaths. In this example, the third breath-window (w3) is the largest breath-window, hence the number of breaths could not be increased, and the apnea feature for w3 is calculated based on the 4 non-BDA breaths. As a result, the apnea features for breath-windows w2 and w3 end up being the same.

In some configurations, the number of windows that can be increased to acquire all required non-BDA breath can be fixed to the size of the largest breath-window to avoid using breaths that are too far in the past, which has little to no relevance to the apnea being classified. If there are less than 2 non-BDA breaths within any breath-window, the apnea feature calculation will not operate because there are not enough breaths to calculate feature statistics for the window.

Apnea-Feature

Figure 10:
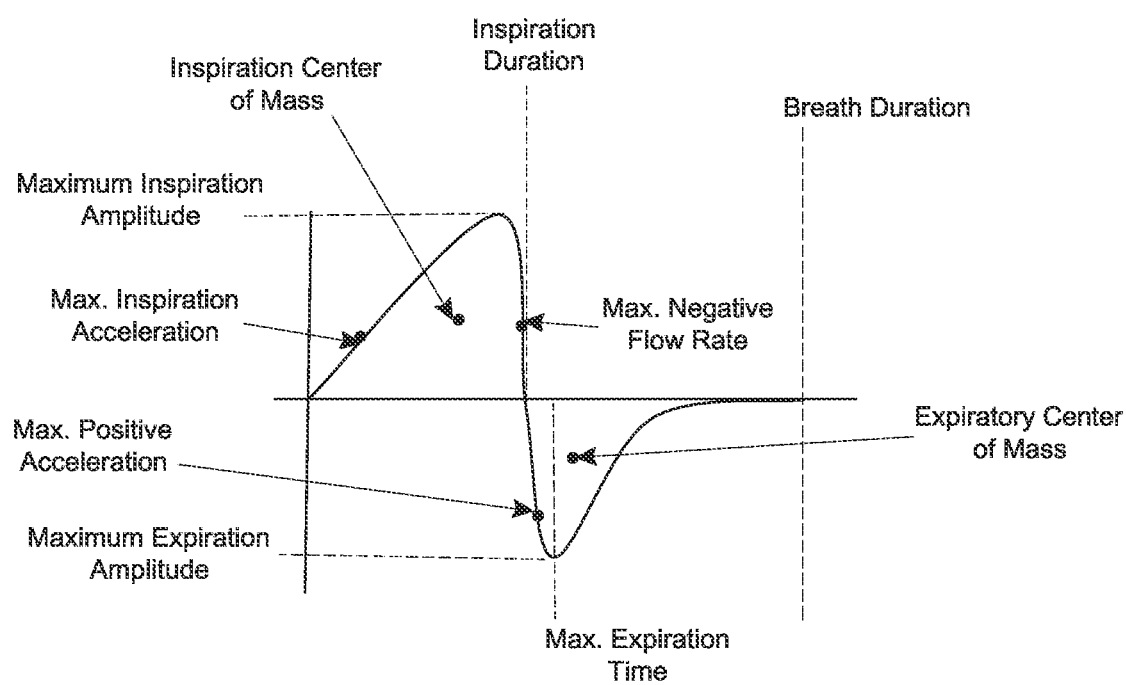
FIG. 10 is a graphical illustration of breath features.

The next step in the illustrated apnea feature calculation is acquiring the values of selected breath features for non-BDA breaths in the breath-window. An example of the breath features is shown in FIG. 10. In some configurations, there are 27 breath features calculated for each valid breath and populated into the breath table. In an embodiment, all 27 features are used. In an embodiment, a subset of features is used. Of course, it should be understood by those of skill in the art that various combinations and sub-combinations of the below listed features or other available features can be used. The features listed are provided by way of illustration and not limitation. In some embodiments, less than all available or used features can be obtained for model training purposes.

Table 1 provides a list of 27 possible breath-features

TABLE 1

Breath features used for development of apnea classification model

| B | Breath Features |
|---|---|
| 1 | Flow Index |
| 2 | Max Inspiration Amplitude |
| 3 | Time of Max Inspiration Amplitude |
| 4 | Breath duration |
| 5 | Inspiration duration |
| 6 | Inspiration duration/Breath duration |
| 7 | Max. Expiration Amplitude |
| 8 | Time of Max Expiration Amplitude |
| 9 | Maximum Expiration Time – Time of Max Inspiration |
| 10 | Maximum Inspiration Amplitude – Maximum Expiration Amplitude |
| 11 | Max. Inspiration Acceleration^ |
| 12 | Time to Max. Inspiration Acceleration^ |
| 13 | Inspiration Volume |
| 14 | Expiration volume |
| 15 | Volume ratio |
| 16 | Amplitude Inspiration Center of Mass (CM) |
| 17 | Time inspiration CM |
| 18 | Amplitude expiration CM |
| 19 | Time Expiration CM |
| 20 | Time Expiration CM – Time Inspiration CM |
| 21 | Amplitude expiration CM – Amplitude Inspiration CM |
| 22 | Maximum Flow Rate * |
| 23 | Time of Maximum Flow Rate* |
| 24 | Time of Maximum negative acceleration^ |
| 25 | Time of the maximum positive acceleration^ |
| 26 | Maximum negative acceleration^ |
| 27 | Maximum positive acceleration^ |

*derived from 1st derivative of the flow signal in an embodiment
^derived from 2nd derivative of the flow signal in an embodiment Breath Feature Normalization and Apnea Feature Statistics The values for the breath features selected for apnea classification are acquired from the breath table for breaths within breath-windows. Then, the breath-features for BDA breaths are removed. Each breath-feature is then divided by the corresponding breath feature of the standard breath to derive normalized breath-features of non-BDA breaths. The mean and standard-deviations of the normalized breath-features are calculated to derive apnea features.

Apnea Feature Vector ($A_F$)

Figure 11:
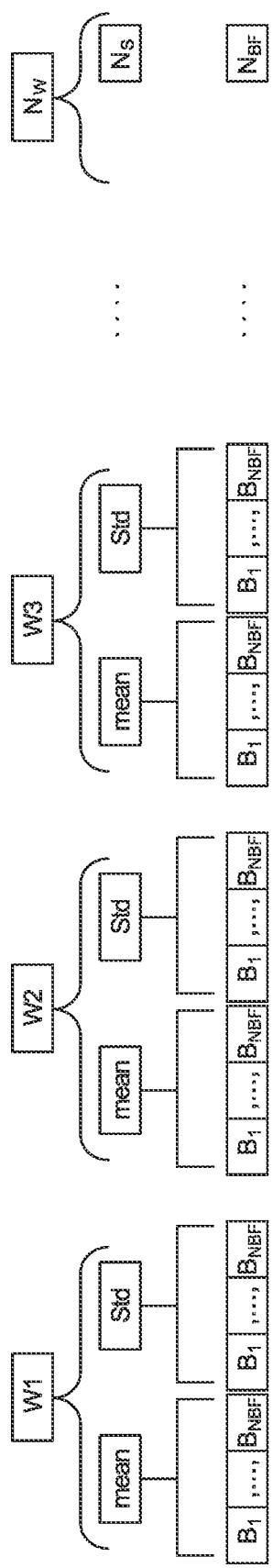
FIG. 11 is a diagram illustrating the formation and population of an apnea feature array.

The apnea-features for each window are stored in memory to form an array of apnea-feature vectors ($A_F$) as shown in FIG. 11. The size of $A_F$, ($N_{AF}$) is a product of the number of breath-features used ($N_{BF}$), the number of breath-windows ($N_w$), and the number of statistical metrics ($N_s$) used to derive the apnea-features:

$$N_{AF} = N_w * N_{BF} * N_s$$

Model Features

Apnea-features derived from empirically obtained data from a large cross section of patients are used for training the apnea classification model during the design phase. The apnea classification model can be trained based on a machine learning algorithm which, in addition to deriving the classification model, also selects a subset of optimal apnea-features (a) from $A_F$. The optimal apnea-features (a) can be used in the final apnea classification model and can be the main output of the apnea feature extraction function.

Apnea Classification

Figure 12:
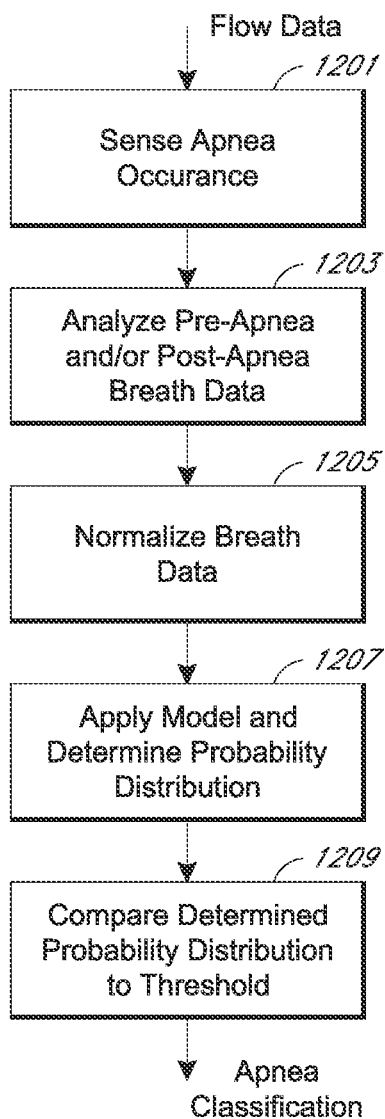
FIG. 12 is an embodiment of an apnea classification flow chart.

To classify a sleep apnea, the apnea-features subset (a) is used in the apnea classification model to derive a probability distribution (PD), which in-turn is compared with a predetermined threshold ($T_{PD}$) to determine the class of the sleep apnea. The flow chart in FIG. 12 outlines an embodiment of an apnea classification process that can be implemented. The process starts at step 1201 where the process senses that an apnea has occurred. At step 1203, the pre-apnea (and/or post-apnea) breath data is analyzed. At step 1205, the analyzed breath data is normalized. The normalized breath data is then applied to a model that has been trained with empirically determined data at step 1207. A probability distribution is determined as explained herein below. The probability distribution is then compared to a threshold at step 1209 in order to determine the apnea classification.

Simple Logistics Apnea Classification

In an embodiment, a simple logistics model is used. The simple logistics model is used as a classifier to provide an output probability distribution for apnea classes. The probability distribution ($PD_{a,OSA}$) of an OSA class given the apnea-features a can be defined by following equation:

$$PD_{a,OSA} = e^{W_{0,OSA} + \sum_{j=1}^{Na} W_{j,OSA} \times a_j} \qquad \text{Equation 1}$$

where $W_{0,OSA}$ is the model bias, $W_{j,osa}$ are the model weights for OSA class, and a is the corresponding apnea-features Similarly, the equation for CSA probability distribution ($PD_{a,CSA}$) is:

$$PD_{a,CSA} = e^{-\left(W_{0,OSA} + \sum_{j=1}^{Na} W_{j,OSA} \times a_j\right)} \qquad \text{Equation 2}$$

The output of each class is then normalized to value from 0 to 1 using the equation below:

$$PD = \frac{PD_{a,OSA}}{PD_{a,OSA} + PD_{a,CSA}} \qquad \text{Equation 3}$$

The PD for a sleep apnea event is then compared with the $T_{PD}$ as shown in Equation 4 to determine the apnea class.

If $PD<0$ OR $PD>1$

Apnea Class=None

Else If $PD>=T_{PD}$

Apnea Class=Obstructive

Else

Apnea Class=Central      Equation 4

Determination of Probability Distribution Threshold ($T_{PD}$)

The $T_{PD}$ can be determined by analyzing the PD for the training dataset calculated by the apnea classification model. $T_{PD}$ can be chosen so that the specificity and sensitivity of the training dataset is as close to each other as possible.

Apnea Classification During Flow Leak

In some configurations, the apnea classification is not performed under a high flow leak condition because apneas may not be detected during leak in certain CPAP device control systems. However, there can be a moment in operation just after the leak has stopped where an apnea occurs with less than the number of breaths required to classify the apnea. In such a situation, the apnea can be classified with breaths that are available at the time. The system can keep track of how many breaths have passed since the leak stopped. If enough breaths have occurred to classify an apnea after the leak has stopped, then the apnea classification system described herein can be used.

Overview of CPAP System

Figure 13:
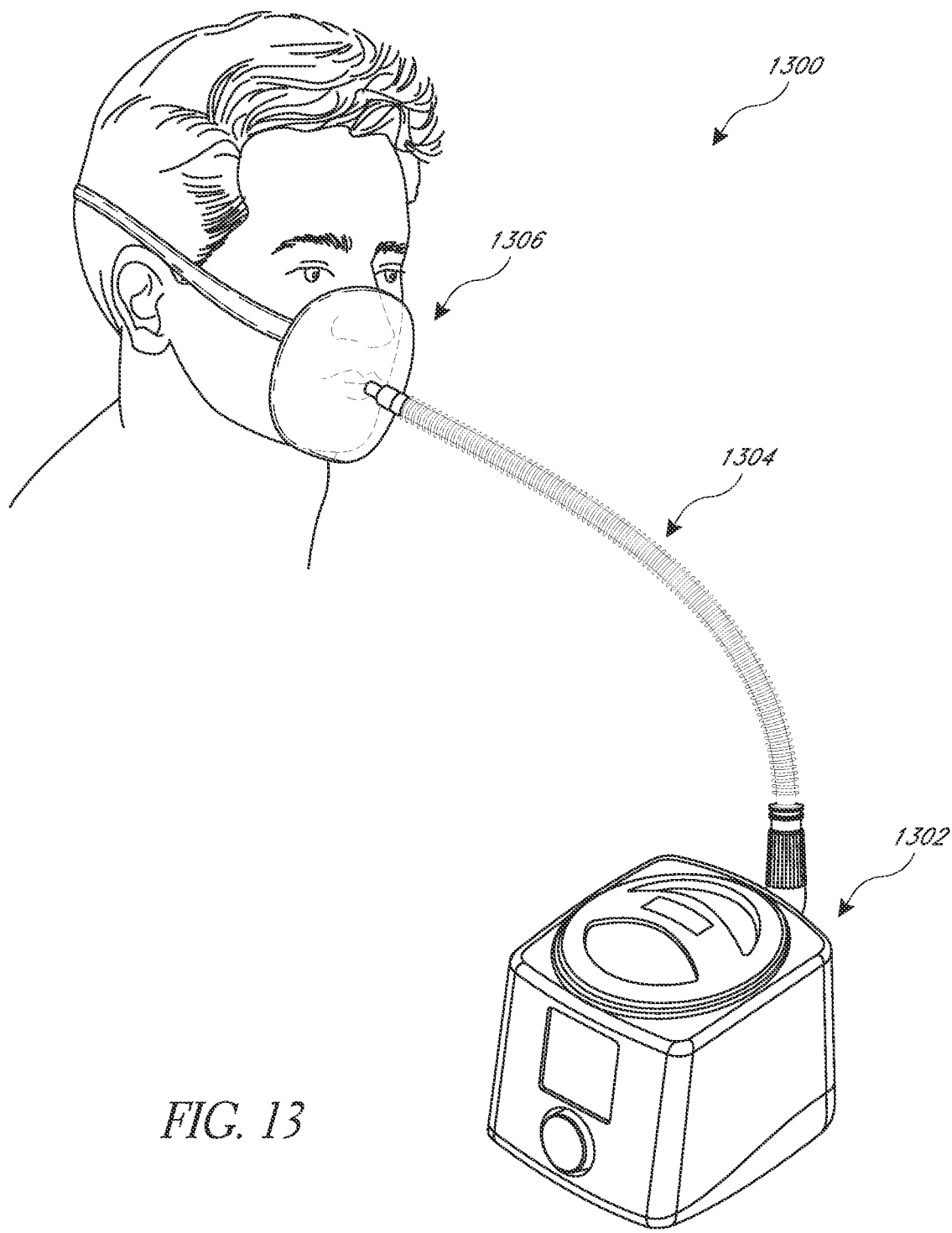
FIG. 13 illustrates an embodiment of a CPAP system.

FIG. 13 illustrates an embodiment of a CPAP system 1300 according to the present disclosure. The system includes a CPAP device 1302, a tube 1304 and a mask 1306. The mask 1306, in use, is positioned over one or both of a nose and face of the patient to supply a positive air pressure thereto. In an embodiment, the CPAP system 1300 also includes a sensor positioned in one or both of the mask 1306 and tube 1304 in order to monitor air flow or pressure there through. In an embodiment, the sensor is a flow sensor placed in the system before the blower or anywhere where flow or pressure information can be obtained. In an embodiment, the sensor is a pressure sensor placed in the system after the blower, but before the humidifier. As will be understood by those of skill in the art, the sensor can be any of a number of sensors located at various locations in the system that are capable of detecting operating characteristics of the system and flow or pressure states of the patient. The CPAP device can be an auto-titrating device, a bi-level device, a single pressure device, or any combination of the afore mentioned CPAP pressure devices.

Figure 14:
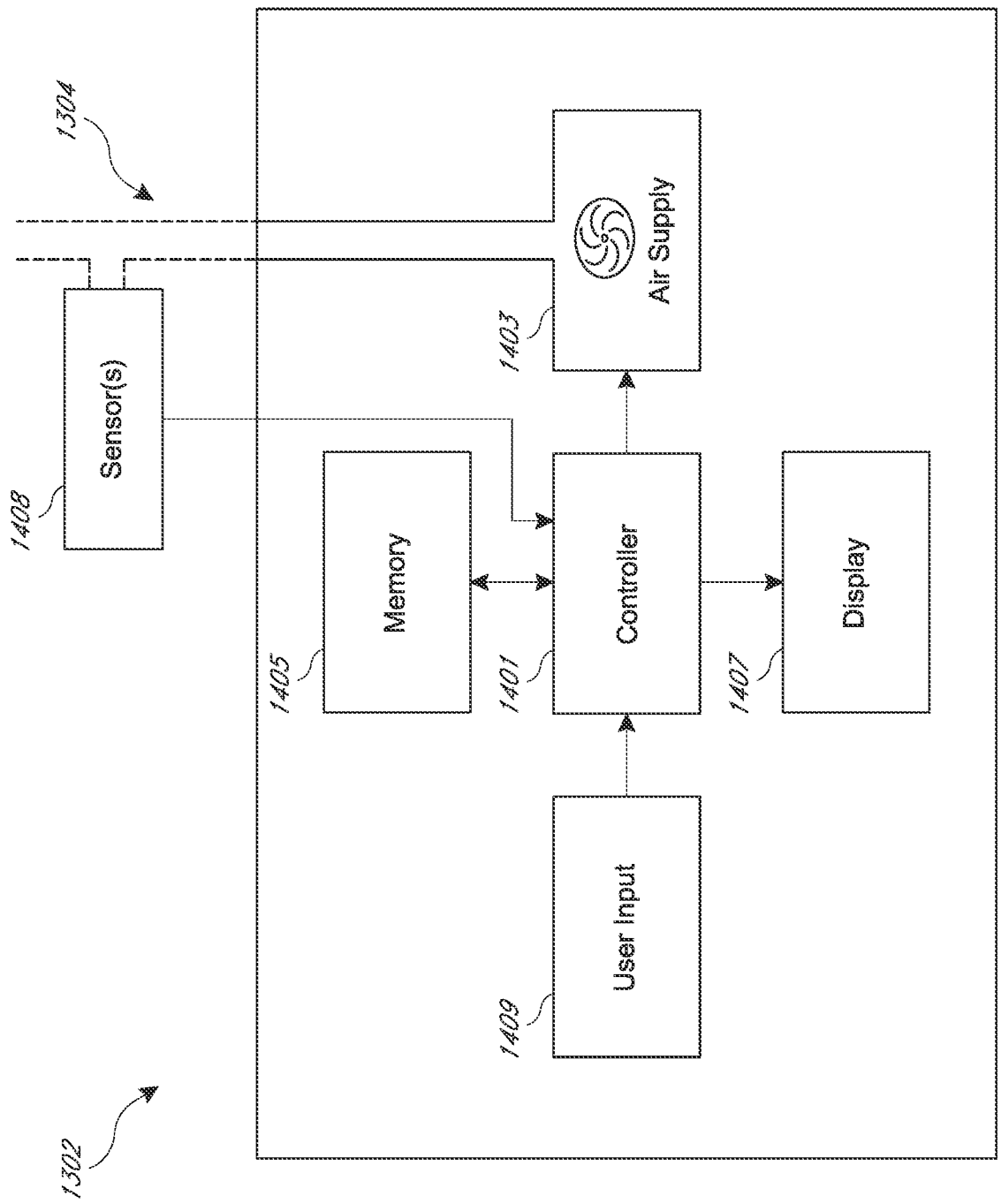
FIG. 14 illustrates an embodiment of hardware components of a CPAP system.

FIG. 14 illustrates a schematic depiction of CPAP device 1302. CPAP device 1302 includes a controller 1401, an air supply 1403, a memory device 1405, and optionally a display 1407 and user inputs 1409. The controller 1401 controls the operation of the CPAP device 1302. The controller 1401 can include, for example, analog or digital processors or other electronic control devices as would be understood by a person of skill in the art from the present disclosure. The controller 1401 controls the operation of the air supply 1403. The controller also receives and analyzes sensor signals from sensor(s) 1408. The controller 1401 communicates with the memory device 1405 to store information including operating information, sensor information, and other information as would be understood by a person of skill in the art and as disclosed herein. The controller can also optionally receive commands from a user input 1409 as well as communicate output information to the display 1407.

CONCLUSION

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art. It will further be appreciated that the data and/or components described above may be stored on a computer-readable medium and loaded into memory of the computing device using a drive mechanism associated with a computer readable storing the computer executable components such as a CD-ROM, DVD-ROM, memory stick, or network interface. Further, the component and/or data can be included in a single device or distributed in any manner. Accordingly, general purpose computing devices may be configured to implement the processes, algorithms and methodology of the present disclosure with the processing and/or execution of the various data and/or components described above.

Although the present invention has been described in terms of certain embodiments, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention.

What is claimed is:

1. A respiratory apparatus comprising:
a pressure or flow sensor for detecting a sensed breath, and
a control system configured to:
analyze one or more apnea features to make a determination whether a detected apnea event is obstructive sleep apnea or central sleep apnea,
wherein the one or more apnea features is derived from the sensed breath by calculating one or more statistical metrics of one or more breath features within one or more predefined breath-windows, each comprising a number of breaths preceding the detected apnea event.

2. The respiratory apparatus of claim 1, wherein the one or more breath features are normalized by dividing the one or more breath features with a corresponding breath feature of a standard breath.

3. The respiratory apparatus of claim 2, wherein the standard breath is a sinusoidal representation of average breath features derived from a local breath-window.

4. The respiratory apparatus of claim 3, wherein the standard breath is derived by fitting two respective sinusoids to average inspiration and expiration measures of breaths in the local breath-window.

5. The respiratory apparatus of claim 4, wherein the two respective sinusoids can be derived from one or more of: 1) mean of maximum flow, 2) mean duration of inspiration, 3) mean minimum flow, and 4) mean total breath duration over the local breath-window.

6. The respiratory apparatus of claim 5, wherein the control system makes the determination by using a trained classifier.

7. The respiratory apparatus of claim 6, wherein the trained classifier uses a simple logistics model.

8. The respiratory apparatus of claim 6, wherein the trained classifier uses a logistics model.

9. The respiratory apparatus of claim 6, wherein the trained classifier uses one or more of a neural network model, logistics model, multiple perception model or support vector machine.

10. The respiratory apparatus of claim 6, wherein the control system classifies the detected apnea event by determining a probability distribution and comparing the probability distribution to a threshold value.

11. The respiratory apparatus of claim 1 wherein the determination is made during the detected apnea event.

12. The respiratory apparatus of claim 1, wherein the control system:
in response to the control system classifying the apnea event as an obstructive sleep apnea, increases a pressure provided by the apparatus; and
in response to the control system classifying the apnea event as a central sleep apnea, maintains or decreases the pressure provided by the apparatus.

13. A method of determining if an apnea is an obstructive sleep apnea or a central sleep apnea, the method comprising:
detecting a sensed breath using a pressure or flow sensor,
deriving one or more apnea features from the sensed breath by calculating one or more statistical metrics of one or more breath features within one or more predefined breath-windows, each comprising a number of breaths preceding the detected apnea event, and
analyzing the one or more apnea features to make a determination whether a detected apnea event is obstructive sleep apnea or central sleep apnea.

14. The method of determining if an apnea is an obstructive sleep apnea or a central sleep apnea of claim 13 further comprising:
in response to the control system classifying the apnea event as an obstructive sleep apnea, increasing a pressure output of a blower; and
in response to the control system classifying the apnea event as a central sleep apnea, maintaining or decreasing the pressure output of a blower.

15. The method of determining if an apnea is an obstructive sleep apnea or a central sleep apnea of claim 13 further comprising normalizing the one or more breath features by dividing the one or more breath features with a corresponding breath feature of a standard breath.

16. The method of determining if an apnea is an obstructive sleep apnea or a central sleep apnea of claim 15, wherein the standard breath is determined by a group of 1 to 12 pre-apnea breaths.

17. The method of determining if an apnea is an obstructive sleep apnea or a central sleep apnea of claim 15, wherein the standard breath is a sinusoidal representation of average breath features derived from a local breath-window.

18. The method of determining if an apnea is an obstructive sleep apnea or a central sleep apnea of claim 17, wherein the standard breath is derived by fitting two respective sinusoids to average inspiration and expiration measures of breaths in the local breath-window.

19. The method of determining if an apnea is an obstructive sleep apnea or a central sleep apnea of claim 18, wherein the two respective sinusoids can be derived from one or more of: 1) mean of maximum flow, 2) mean duration of inspiration, 3) mean minimum flow, and 4) mean total breath duration over the local breath-window.

20. The method of determining if an apnea is an obstructive sleep apnea or a central sleep apnea of claim 19, wherein the control system makes the determination by using a trained classifier.

\* \* \* \* \*

UNITED STATES PATENT AND TRADEMARK OFFICE
CERTIFICATE OF CORRECTION

PATENT NO. : 12,214,125 B2
APPLICATION NO. : 17/303161
DATED : February 4, 2025
INVENTOR(S) : David Robin Whiting et al.

It is certified that error appears in the above-identified patent and that said Letters Patent is hereby corrected as shown below:

In the Specification

In Column 4, Line 33, delete "is repeated" and insert --is repeated.--.

In Column 7, Line 62, delete "window (w1) requires" and insert --window ($w_1$) requires--.

In Column 7, Line 65, delete "window (w2) requires" and insert --window ($w_2$) requires--.

In Column 7, Line 66, delete "window (w3) is" and insert --window ($w_3$) is--.

In Column 8, Line 1, delete "for w3 is" and insert --for $w_3$ is--.

In Column 8, Line 3, delete "windows w2 and w3 end" and insert --windows $w_2$ and $w_3$ end--.

In Column 8, Line 58 (Approx.), delete "from 1st derivative" and insert --from $1^{st}$ derivative--.

In Column 8, Line 59 (Approx.), delete "from 2nd derivative" and insert --from $2^{nd}$ derivative--.

In Column 9, Line 43, delete "distribution ($PD_{a,oSA}$) of" and insert --distribution ($PD_{a,OSA}$) of--.

In Column 9, Line 50 (Approx.), delete "where $W_{0,OSA}$ is" and insert --where $W_{0,OSA}$ is--.

Signed and Sealed this
Eighth Day of April, 2025

Coke Morgan Stewart
*Acting Director of the United States Patent and Trademark Office*